US010494923B2

(12) United States Patent
Lawson et al.

(10) Patent No.: US 10,494,923 B2
(45) Date of Patent: Dec. 3, 2019

(54) METHOD TO PERFORM HYDROCARBON SYSTEM ANALYSIS FOR EXPLORATION, PRODUCTION AND DEVELOPMENT OF HYDROCARBONS

(71) Applicants: Michael Lawson, Spring, TX (US); Brian K. Peterson, Fogelsville, PA (US); Cara L. Davis, Houston, TX (US); Michael J. Formolo, The Woodlands, TX (US); Isolde Belien, Kingwood, TX (US); Lori L. Summa, Houston, TX (US); Robert J. Pottorf, Houston, TX (US)

(72) Inventors: Michael Lawson, Spring, TX (US); Brian K. Peterson, Fogelsville, PA (US); Cara L. Davis, Houston, TX (US); Michael J. Formolo, The Woodlands, TX (US); Isolde Belien, Kingwood, TX (US); Lori L. Summa, Houston, TX (US); Robert J. Pottorf, Houston, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 1097 days.

(21) Appl. No.: 14/844,130

(22) Filed: Sep. 3, 2015

(65) Prior Publication Data

US 2016/0084081 A1    Mar. 24, 2016

Related U.S. Application Data

(60) Provisional application No. 62/052,317, filed on Sep. 18, 2014.

(51) Int. Cl.
*E21B 49/08* (2006.01)
*G01N 33/24* (2006.01)
(Continued)

(52) U.S. Cl.
CPC ........ *E21B 49/088* (2013.01); *E21B 41/0092* (2013.01); *E21B 47/065* (2013.01); *G01N 33/24* (2013.01)

(58) Field of Classification Search
CPC .. E21B 49/088; E21B 41/0092; E21B 47/065; G01N 33/24; G01N 33/241; G01V 9/007
See application file for complete search history.

(56) References Cited

U.S. PATENT DOCUMENTS 5,388,456 A    2/1995  Kettel
6,613,520 B2   9/2003  Ashby
(Continued)

FOREIGN PATENT DOCUMENTS

WO    WO 2007/008932    1/2007

OTHER PUBLICATIONS

Wang, Y., et al., "Thermal cracking history by laboratory kinetic simulation of Paleozoic oil in eastern Tarim Basin, NW China, implications for the occurrence of residual oil reservoirs," *Organic Geochemistry* 65, ScienceDirect, Elsevier, pp. 1803-1815 (2006).
(Continued)

*Primary Examiner* — Yong-Suk Ro
(74) *Attorney, Agent, or Firm* — ExxonMobil Upstream Research Company—Law Department

(57) ABSTRACT

A method and system are provided for exploration, production and development of hydrocarbons. The method involves analyzing a sample for a geochemical signature, which includes a multiply substituted isotopologue signature and/or a position specific isotope signature. Then, historical temperatures are determined based on the signature. The historical temperature is used to define seal timing, trap timing, migration efficiency and/or charge efficiency, which is used to develop or refine an exploration, development, or production strategy.

24 Claims, 6 Drawing Sheets

(51) Int. Cl.
E21B 41/00 (2006.01)
E21B 47/06 (2012.01)

(56) References Cited

U.S. PATENT DOCUMENTS

| | | | |
|---|---|---|---|
| 7,124,030 B2 | 10/2006 | Ellis | |
| 7,174,254 B2 | 2/2007 | Ellis | |
| 7,529,626 B1 | 5/2009 | Ellis | |
| 8,071,295 B2 | 12/2011 | Ashby | |
| 8,073,663 B2* | 12/2011 | Carruthers | G01V 1/30 703/10 |
| 8,316,934 B2* | 11/2012 | Pietrobon | E21B 43/14 166/250.01 |
| 8,476,016 B2 | 7/2013 | Ashby | |
| 8,505,375 B2 | 8/2013 | Smalley | |
| RE44,728 E | 1/2014 | Pope et al. | |
| 8,760,657 B2 | 6/2014 | Pope et al. | |
| 8,950,251 B2 | 2/2015 | Valentine | |
| 2008/0147326 A1 | 6/2008 | Ellis | |
| 2008/0299635 A1* | 12/2008 | Pfeiffer | E21B 43/40 435/167 |
| 2011/0250582 A1 | 10/2011 | Gates et al. | |
| 2011/0264430 A1* | 10/2011 | Tapscott | G01V 99/00 703/10 |
| 2012/0134749 A1 | 5/2012 | Darrah | |
| 2013/0037707 A1* | 2/2013 | Lamberti | G01N 33/241 250/282 |
| 2013/0091925 A1 | 4/2013 | Darrah et al. | |
| 2013/0103337 A1 | 4/2013 | Eiler | |
| 2013/0116126 A1 | 5/2013 | Ashby et al. | |
| 2014/0011692 A1 | 1/2014 | Ashby | |
| 2014/0138528 A1 | 5/2014 | Pope et al. | |
| 2014/0162274 A1 | 6/2014 | Kunin et al. | |
| 2014/0256055 A1* | 9/2014 | Pottorf | G01V 9/007 436/163 |
| 2015/0038348 A1 | 2/2015 | Ashby et al. | |

OTHER PUBLICATIONS

Berner, U., et al. (1988), "Maturity Related Mixing Model for Methane, Ethane and Propane, Based on Carbon Isotopes", Advances in Organic Geochemistry, vol. 13, Nos. 1-3, pp. 67-72.
Stahl, W.J., (1977), "Carbon and Nitrogen Isotopes in Hydrocarbon Research and Exploration", Chemical Geology, vol. 20, pp. 121-149.
Chung, H.M., et al., (1979), "Use of Stable Carbon Isotope Compositions of Pyrolytically Derived Methane As Maturity Indices For Carbonaceous Materials", Geochimica et Cosmochimica Acta, vol. 43, pp. 1979-1988.
James, A.T., (1990), "Correlation of Reservoired Gases Using the Carbon Isotopic Compositions of Wet Gas Components, The American Association of Petroleum Geologists Bulletin", vol. 74, No. 9, pp. 1441-1458.
Whiticar, M.J., (1996), "Stable Isotope Geochemistry of Coals, Humic Kerogens and Related Natural Gases", vol. 32, pp. 191-215.
Stolper, D.A., et al. (2014), "Formation Temperatures of Thermogenic and Biogenic Methane", Science, vol. 344, pp. 1500-1503.
Stolper, D.A., et al., (2014), "Combined 13C—D and D—D Clumping in Methane: Methods and Preliminary Results", Geochimica et Cosmochimica Acta, vol. 126, pp. 169-191.
Urey. H.C., et al., (1933), "Some Thermodynamic Properties of the H1H2, H2H2 Molecules and Compounds Containing The H2 Atom", Journal of Chemical Physics, vol. 1, pp. 137-143.
Bigeleisen, J., et al., (1947): "Calculation of Equilbrium Constants for Isotopic Exchange Reactions", The Journal of Chemical Physics, vol. 15, No. 5., pp. 261-267.
Richet, R., et al., (1977), "A Review of Hydrogen, Carbon, Nitrogen, Oxygen, Sulphur, and Chlorine Stable Isotope Fractionation Among Gaseous Molecules", Ann. Rev. Earth Planet. Sci., vol. 5, pp. 65-110.
Vidler, M., et al., (2000), "Accurate Partition Function and Thermodynamic Data for Water", Journal of Chemical Physics, vol. 113, No. 21, pp. 9766-9771.
Liu, Q., et al., (2010), "On the Proper Use of The Bigeleisen-Mayer Equation and Corrections to it in the Calculation of Isotopic Fractionation Equilibrium Constants", Geochimica et Cosmochimica Acta, vol. 74, pp. 6965-6983.
Bloino, J., et al., (2012), "General Perturbative Approach for Spectroscopy: Thermodynamics, and Kinetics: Methodological Background and Benchmark Studies", J. Chem. Theory Comput., vol. 8, pp. 1015-1036.
Truhlar, D.G., et al., (1991), "Simple Perturbation Theory Estimates of Equilibrium Constants From Force Fields", J. Chem. Phys., vol. 94 (1), pp. 357-359.
Webb, M.A., et al., (2014), "Position-Specific and Clumped Stable Isotope Studies: Comparison of The Urey and Path-Integral Approaches for Carbon Dioxide, Nitrous Oxide, Methane, and Propane", J. Phys. Chem. A, vol. 118, pp. 467-474.
Rustad, J.R., et al., (2010), "Calculation of Boron-Isotope Fractionation Between B(OH)3(aq) and B(OH)4-(aq)", Geochimica et Cosmochimica Acta, vol. 74, pp. 2843-2850.
Wang. Y., et al., (2009), "Equilibrium 2H/1H Fractionations in Organic Moldecules: I. Experimental Calibration of Ab Initio Calculations", Geochimica et Cosmochimica Acta, vol. 73, pp. 7060-7075.
Reeves, E.P., et al., (2012), "Hydrogen Isotope Exchange Between n-Alkanes and Water Under Hydrothermal Conditions", Geochimica et Cosmochimica Acta, vol. 77, pp. 582-599.
Glasstone, S., et al., (1941), "The Theory of Rate Processes", McGraw-Hill, New York, pp. 249.
Burnham, A.K., et al., (1989): "A Chemical Kinetic Model of Vitrinite Maturation and Reflectance", Geochimica et Cosmochimica Acta, vol. 53, pp. 2649-2657.
Sweeney, J. J., et al., (1990), "Evaluation of a Simple Model of Vitrinite Reflectance Based on Chemical Kinetics", The American Association of Petroleum Geologists Bulletin, vol. 74, No. 10, pp. 1559-1570.
Magoon, L.B., et al., (1994), "The Petroleum System—From Source to Trap", AAPG Memoir 60, pp. 3-24.
Rustad, J.R., et al., (2007); "Ab Initio Calculation of Isotopic Fractionation in B(OH)3(aq) and BOH4-(aq)", JACS Communications, pp. 2222-2223.
Mudford, B. et al., "Timing of hydrocarbon generation and accumulation in fault-bounded compartments in the Norphlet Formation, offshore Alabama," *Marine and Petroleum Geology* 12(5), pp. 549-558 (1995).
Hassanzadeh, G. et al., "Petroleum System Analysis Using Geochemical Studies, Isotope and 1D Basin Modeling in Hendijan Oil Field, SW Iran," International Petroleum Technology Conf., IPTC 14797, Bangkok, Thailand, 11 pgs. (Feb. 7-9, 2012).
Lee, G.H. et al., "Timing of trap formation in the southwestern margin of the Ulleung Basin, East Sea (Japan Sea) and implications for hydrocarbon accumulations," *Geosciences Journal* 8(4), pp. 369-380 (Dec. 2004).
Stolper, A., "New Insights into the Formation and Modification of Carbonate-Bearing Minerals and Methane Gas in Geological Systems Using Multiply Substituted Isotopologues," Thesis, California Institute of Technology, Part 1, pp. 1-77 (Defended May 13, 2014).
Stolper, A., "New Insights into the Formation and Modification of Carbonate-Bearing Minerals and Methane Gas in Geological Systems Using Multiply Substituted Isotopologues," Thesis, California Institute of Technology, Part 2, pp. 78-161 (Defended May 13, 2014).
Stolper, A., "New Insights into the Formation and Modification of Carbonate-Bearing Minerals and Methane Gas in Geological Systems Using Multiply Substituted Isotopologues," Thesis, California Institute of Technology, Part 3, pp. 162-245 (Defended May 13, 2014).
Stolper, A., "New Insights into the Formation and Modification of Carbonate-Bearing Minerals and Methane Gas in Geological Systems Using Multiply Substituted Isotopologues," Thesis, California Institute of Technology, Part 4, pp. 246-305 (Defended May 13, 2014).

(56) References Cited

OTHER PUBLICATIONS

Xiao, X.M. et al., "Tracing of deeply-buried source rock: A case study of the WC9-2 petroleum pool in the Pearl River Mouth Basin, South China Sea," *Marine and Petroleum Geology* 26, pp. 1365-1378 (2009).

* cited by examiner

METHOD TO PERFORM HYDROCARBON SYSTEM ANALYSIS FOR EXPLORATION, PRODUCTION AND DEVELOPMENT OF HYDROCARBONS

CROSS-REFERENCE TO RELATED APPLICATION

This application claims the benefit of U.S. Provisional Patent Application 62/052,317 filed Sep. 18, 2014 entitled METHOD TO PERFORM HYDROCARBON SYSTEM ANALYSIS FOR EXPLORATION, PRODUCTION AND DEVELOPMENT OF HYDROCARBONS, the entirety of which is incorporated by reference herein.

FIELD OF THE INVENTION

Embodiments of the present disclosure relate generally to the field of geochemistry and basin modeling. More particularly, the present disclosure relates to systems and methods for determining the presence and timing of key hydrocarbon system components (e.g. source rock presence, timing and extent of maturation, migration efficiency, trap timing, seal timing and adequacy, etc.) that can be used to develop exploration, development and production strategies.

BACKGROUND

This section is intended to introduce various aspects of the art, which may be associated with exemplary embodiments of the present disclosure. This discussion is believed to assist in providing a framework to facilitate a better understanding of particular aspects of the present invention. Accordingly, it should be understood that this section should be read in this light, and not necessarily as admissions of prior art.

The major components and processes associated with the presence of subsurface hydrocarbon accumulations in a sedimentary basin include (1) the presence of a source rock from which hydrocarbons can be generated, (2) the burial of the source rock to sufficient temperatures and pressures to result in the generation and expulsion of liquid and/or gaseous hydrocarbons from a source rock (source maturity), (3) presence of a reservoir of sufficient adequacy to store hydrocarbons, (4) migration of liquid and/or gaseous hydrocarbons to and accumulation in a reservoir, and (5) a trap and a seal that prevents significant leakage of hydrocarbons from the reservoir. The relative timing of each of these components and processes are utilized to determine the existence of any accumulation. Each of these components should be present for a subsurface hydrocarbon accumulation to exist.

The presence of some of these components can be addressed adequately using conventional techniques including by direct observation. For example, the presence of hydrocarbons at a seep location or in subsurface sediments suggests the presence of a source rock that has reached sufficient depths to generate hydrocarbons and that these hydrocarbons have been expulsed from the source. Similarly, during drilling of a well reservoir lithologies may be encountered that confirm the presence of a reservoir. Though helping to confirm presence, such evidence alone typically provides insufficient information to develop exploration, production, and development strategies. For example, if multiple source rocks are present in the subsurface, the presence of hydrocarbons at a seep or in the subsurface may not provide the information necessary to determine which source rock has generated the hydrocarbons.

In addition to direct observations techniques, modeling, such as basin modeling, can be used to provide estimates on some of these components. For example, basin modeling can be used to predict the time in the past that source rocks reached sufficient temperatures to generate hydrocarbons, and can further be used to predict how much and what type of hydrocarbons (e.g., oil and/or gas) were generated through some knowledge of the depths and temperatures the source rock reached as well as characteristics of the source rock. This information can be provided by direct temperature information (e.g., fluid inclusions present with source intervals that may or may not have been uplifted can be used to provide a minimum temperature that a source rock has experienced). Alternatively, the composition of hydrocarbons sampled in the subsurface or at the surface can be used to determine what maturities source rocks have reached when the hydrocarbons have a common origin from one source interval. Those maturities are a function of the time and temperature of burial, and therefore provide an indirect estimate of temperature history. However, significant uncertainty results when direct temperature information from the source rock is not available or when sampled hydrocarbons represent mixtures of hydrocarbons that were produced from different source intervals within the subsurface. Given this uncertainty, it can often be difficult to determine the timing of source rock maturation and migration of hydrocarbons. In addition, it is typically very difficult to determine the timing of trap structure presence, and the timing of adequate seal presence given the lack of direct measures or indicators of these components. Further still, it is often difficult to determine, in any systems where multiple source rocks are potentially present, which source rock is responsible for the generation of hydrocarbons that may ultimately migrate to an accumulation. Addressing such questions may de-risk the components of a hydrocarbon system. Such information can then be used to explore for hydrocarbons both on a local and regional basis.

As such, there is a need for enhanced techniques that may effectively determine the presence, timing and quality or efficiency of components within the hydrocarbon system. In particular, efficient and cost effective methods for determining (1) the maturity or temperatures that source rocks have experienced during burial and the time at which source rock(s) reach maturities (e.g., temperatures and pressures) sufficient to generate hydrocarbons, (2) the timing of migration, or charge, of hydrocarbons into a reservoir, and (3) the timing of trap and adequate seal presence may provide a valuable tool that could be used in hydrocarbon exploration at various business stages, from frontier exploration to extension of proven plays or high-grading prospects in proven plays through field development and exploitation.

SUMMARY

According to disclosed aspects and methodologies, a method for exploration, production and development of hydrocarbons is described. The method comprises obtaining a sample comprising hydrocarbons associated with a subsurface source interval; analyzing the sample for a geochemical signature, wherein the geochemical signature comprises one or more of a multiply substituted isotopologue signature and a position specific isotope signature for a one or more specific hydrocarbon compound; determining one or more historical temperatures based on the one or more of multiply substituted isotopologue signature and position specific isotope signature; defining one or more of seal timing, trap timing, migration efficiency and charge efficiency based on the determined one or more historical temperatures; and developing or refining an exploration, development, or production strategy based on the defined one or more of seal timing, trap timing, migration efficiency and charge efficiency. The method may also be utilized to produce hydrocarbons based on the exploration, development, or production strategy.

In yet another embodiment, a computer system for exploration, production and development of hydrocarbons is described. The computer system comprises a processor; memory in communication with the processor; and a set of instructions stored in memory and accessible by the processor. The set of instructions, when executed by the processor, are configured to: analyze a hydrocarbon sample associated with a subsurface source interval for a geochemical signature, wherein the geochemical signature comprises one or more of a multiply substituted isotopologue signature and a position specific isotope signature for a one or more specific hydrocarbon compound; determine one or more historical temperatures based on the one or more of multiply substituted isotopologue signature and position specific isotope signature; define one or more of seal timing, trap timing, migration efficiency and charge efficiency based on the determined one or more historical temperatures; and develop or refine an exploration, development, or production strategy based on the defined one or more of seal timing, trap timing, migration efficiency and charge efficiency.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION

Figure 1:
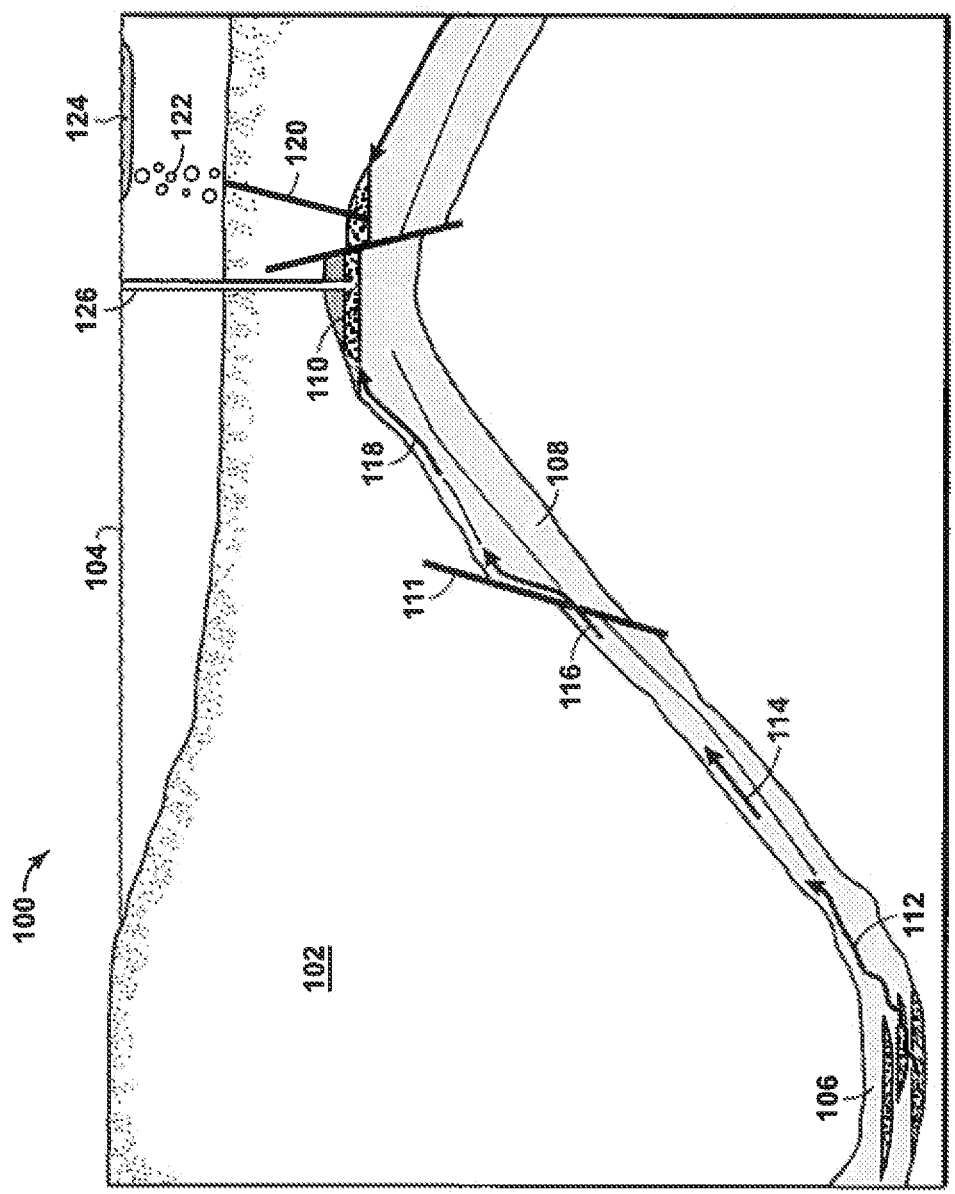
FIG. 1 is a side elevational view of components of a hydrocarbon system in a subsurface region.

In the following detailed description section, the specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the disclosure is not limited to the specific embodiments described below, but rather, it includes all alternatives, modifications, and equivalents falling within the true spirit and scope of the appended claims.

Various terms as used herein are defined below. To the extent a term used in a claim is not defined below, it should be given the definition persons in the pertinent art have given that term in the context in which it is used.

As used herein, "a" or "an" entity refers to one or more of that entity. As such, the terms "a" (or "an"), "one or more", and "at least one" can be used interchangeably herein unless a limit is specifically stated.

As used herein, the terms "comprising," "comprises," "comprise," "comprised," "containing," "contains," "contain," "having," "has," "have," "including," "includes," and "include" are open-ended transition terms used to transition from a subject recited before the term to one or more elements recited after the term, where the element or elements listed after the transition term are not necessarily the only elements that make up the subject.

As used herein, "exemplary" means exclusively "serving as an example, instance, or illustration." Any embodiment described herein as exemplary is not to be construed as preferred or advantageous over other embodiments.

As used herein "hydrocarbons" are generally defined as molecules formed primarily of carbon and hydrogen atoms such as oil and natural gas. Hydrocarbons may also include other elements or compounds, such as, but not limited to, halogens, metallic elements, nitrogen, oxygen, sulfur, hydrogen sulfide (H2S) and carbon dioxide (CO2). Hydrocarbons may be produced from hydrocarbon reservoirs through wells penetrating a hydrocarbon containing formation. Hydrocarbons derived from a hydrocarbon reservoir may include, but are not limited to, petroleum, kerogen, bitumen, pyrobitumen, asphaltenes, tars, oils, natural gas, or combinations thereof. Hydrocarbons may be located within or adjacent to mineral matrices within the earth, termed reservoirs. Matrices may include, but are not limited to, sedimentary rock, sands, silicilytes, carbonates, diatomites, and other porous media.

As used herein, "hydrocarbon production" refers to any activity associated with extracting hydrocarbons from a well or other opening. Hydrocarbon production normally refers to any activity conducted in or on the well after the well is completed. Accordingly, hydrocarbon production or extraction includes not only primary hydrocarbon extraction but also secondary and tertiary production techniques, such as injection of gas or liquid for increasing drive pressure, mobilizing the hydrocarbon or treating by, for example chemicals or hydraulic fracturing the wellbore to promote increased flow, well servicing, well logging, and other well and wellbore treatments.

As used herein the term "isotope" refers to one of two or more atoms with the same atomic number but with different numbers of neutrons. Hydrocarbon molecules may contain a variety of isotopes. Hydrocarbon molecules contain both carbon and hydrogen atoms. Carbon can be present in the molecule as one of two stable isotopes: $^{12}C$, which has 6 protons and 6 neutrons (shown herein as C); and, in much lower concentrations, $^{13}C$, which has 6 protons and 7 neutrons. Similarly, hydrogen can be present in a molecule as one of two stable isotopes: H, which contains 1 proton but no neutron; and, in much lower concentrations, Deuterium (D), which has 1 proton and 1 neutron.

As used herein, the term "hydrocarbon system" refers to the relationships between required components and the processes required for the presence of any subsurface hydrocarbon accumulation as described by Magoon and Dow. See, e.g., Magoon and Dow, The Petroleum System—from source to trap: AAPG Memoir 60, pp. 3-24 (1994).

As used herein the term "hydrocarbon system component" refers to items that are present for the presence of a subsurface hydrocarbon accumulation, comprising one or all of a source rock, reservoir rock, a seal rock, and overburden rock.

As used herein, the term "hydrocarbon system processes" refers to events that are present for the presence of any subsurface hydrocarbon accumulation, comprising trap formation and the generation-migration-accumulation of hydrocarbons.

As used herein the term "historical temperature", refers to any temperature from the point of generation of the hydrocarbon to the temperature at the point of extraction from the reservoir.

As used herein the term "basin modeling", refers generally to any method or analysis, computerized or otherwise, that provides a representation of the history of a sedimentary basin or other subsurface section of interest and/or an estimate of timing of any component of a hydrocarbon system (including but not limited to a burial history, time a specific subsurface location or layer reached a certain temperature or maturity, or for how long a location was in a certain temperature range, timing of expulsion, migration, accumulation etc.). Generally a basin model is based on and/or constrained by measured or derived data representing present day conditions (e.g. stratigraphy, current bottom hole temperature, heat flow) or a condition in the past (e.g. water depth) on which a model of the past history of the area of interest is based. The calculations may be performed using a processor or other computer system.

As used herein the term "signatures" refers to the relative abundances, concentrations and/or ratios of various elements, isotopes, positions within a compound and isotopologues of a given species.

As used herein the term "isotopologue" refers generally to molecules that have the same chemical composition, but have a different isotopic signature. For example, methane contains 1 atom of carbon and four atoms of hydrogen. Each atom in the methane structure can contain one of the two stable isotopes of that atom, and as such there are 10 possible isotopologues of methane.

As used herein the term "multiply substituted isotopologue" refers generally to an isotopologue that contains at least two rare isotopes in its structure. For example, a multiply substituted methane isotopologue must contain one $^{13}C$ atom and one D atom, or at least 2 D atoms in the absence of a $^{13}C$ atom.

As used herein the term "clumped isotopologue" refers generally to an isotopologue that contains at least two rare isotopes that share a common chemical bond in its structure. For example, a clumped isotopologue of methane must one $^{13}C$ atom that shares a chemical bond with at least one D atom.

As used herein the term "position specific isotope effect" refers generally to a compound that has multiple positions for a rare isotope to reside. For example, a position specific isotope effect in propane could refer to the position of the $^{13}C$ atom, which can be positioned either at the center of the compound or one of the end positions, or the position of the D atom, which can be attached to either a central or end position carbon.

As used herein the term "stochastic distribution" refers generally to a system where the stable isotopes in a given population of molecules are distributed randomly among all possible isotopologues of a given species. This stochastic distribution is the reference frame from which deviations are measured and is used to provide a baseline to identify anomalies that may be associated with secondary isotope exchange processes.

While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks. While the figures illustrate various serially occurring actions, it is to be appreciated that various actions could occur concurrently, substantially in parallel, and/or at substantially different points in time.

In the following section, specific embodiments of the present techniques are described in connection with disclosed aspects and techniques. However, to the extent that the following description is specific to a particular aspect, technique, or a particular use, this is intended to be for exemplary purposes only. Accordingly, the invention is not limited to the disclosed aspects and techniques described below, but rather includes all alternatives, modifications, and equivalents falling within the scope of the appended claims.

According to aspects of the disclosed methodologies and techniques, the multiply substituted isotopologue signatures and/or position specific isotope effects or signatures of single or numerous co-existing isotopologues of hydrocarbons can be integrated with results from direct or indirect measurements of temperature (e.g. fluid inclusions, molecular geochemistry) and/or results from basin modeling to determine presence and timing of one or more components in hydrocarbon system analysis to develop or refine exploration, development, or production strategies. In particular, these disclosed methodologies and techniques may be used to determine components, such as (i) the presence of source rock(s), (ii) timing and extent of source rock maturation, and (iii) presence and timing of trap and/or adequate seal presence.

In one or more embodiments, the present techniques may include combining clumped isotopic signatures of hydrocarbon compounds (e.g., $CH_4$, $C_2H_6$, or $C_3H_8$) with elemental, molecular, and isotopic signatures obtained from gas, oil, water and fluid inclusion samples. The use of multiply substituted isotopologue geochemistry may enhance the ability to de-risk specific aspects of the hydrocarbon system. When combined and integrated with traditional geochemical techniques, such as molecular (e.g., methane, ethane, carbon dioxide, or nitrogen), bulk (e.g., mixtures of gases), stable isotope geochemistry (e.g., carbon, hydrogen, nitrogen, or sulfur) of hydrocarbon and non-hydrocarbon gases, molecular geochemistry of oils (e.g. saturate and aromatic compounds), physical measurements (e.g., pressure, volume, and temperature (PVT), and results from basin modeling approaches (e.g. thermal histories of particular lithologies, yield of hydrocarbons as a function of time or temperature) these techniques provide enhancements to hydrocarbon system analysis to determine the timing of trap and/or adequate seal presence or timing of maturation of the source rocks when presence and timing of other aspects of the hydrocarbon system are already known. That is, the integration of this clumped isotopic signature and/or position specific isotope signature (e.g., different geochemical tracer) with existing geochemical and modeling approaches may be utilized to perform hydrocarbon system analysis to develop local and regional exploration programs. The development of these local and regional exploration programs may be based on an understanding of how much hydrocarbon has been generated and when versus when traps and adequate seals were present, an understanding of the potential fetch areas and potential connected volumes of hydrocarbons in the subsurface, relationships between nearby accumulations given an understanding of absolute and relative timing of hydrocarbon generation and trap and seal timing between the different accumulations, and the migration history and direction and/or migration and charge efficiency. This technology provides a mechanism to alter exploration, development, and production strategies to maximize the volumes of hydrocarbon ultimately produced.

Multiply substituted isotopologue geochemistry is based on the variation in the distribution of isotopes within a molecule that gives rise to molecules that are identical in their elemental composition, but that may differ in the isotopic composition of individual atoms within that molecule. These species are called isotopologues. For example, there are three isotopologues of nitrogen (e.g., $^{14}N_2$, $^{15}N^{14}N$, and $^{15}N_2$). An isotopologue in which two or more rare isotopes are present in close proximity (i.e., isotopic "clumps") is called a multiply-substituted isotopologue or clumped isotope (e.g., $^{15}N_2$). The hydrocarbon isotopologues involve hydrocarbon compounds, which contain carbon and hydrogen atoms that have natural isotopes of $^{12}C$, $^{13}C$, $^{1}H$, or H (deuterium or D). $^{12}C$ represents 98.93 mole percent (mol. %) of the total carbon on Earth, while $^{13}C$ forms the remaining 1.07 mol. %. Similarly, the isotopic abundance of $^{1}H$ on earth is 99.985 mol. % while D has an abundance of 0.015 mol. %. Common volatile hydrocarbons have large numbers of isotopologues (e.g., methane has 10; ethane has 21; propane has 36). Common isotopologues of methane for example include $^{13}C^{1}H_3D$ or $^{12}C^{1}H_4$. In addition to the number of rare isotopes, the distribution of isotopes in the molecule can also provide information. For example, in a hydrocarbon compound with three carbon atoms, the rare isotope can take either a central or terminal (end of the molecule) position. Similarly, rare isotopes of hydrogen can occupy different positions. As the size of the hydrocarbon compound increases, so does the number of positions that these rare isotopes can be situated. This effect is called the position specific isotope effect, or isotopomer geochemistry.

The multiply substituted isotopologue signature and the position specific isotope signature of any molecule is a function of (i) temperature-independent randomly populated processes (e.g., stochastic distribution) and (ii) other non-random mass fractionating processes. The stochastic distribution of any isotopologues can be determined from the bulk isotope signatures of the species from which it derives. For example, determining the stochastic distribution of isotopologues for methane involves knowledge of the $\delta^{13}C$ and $\delta D$ signatures of methane. Under equilibrium conditions, the non-random processes may be temperature-time dependent isotopic exchange reactions in some hydrocarbons. For example, multiply substituted isotopologue signatures in methane appear to provide equilibrium gas generation temperatures (See, e.g., (2014) Stolper et al., Formation temperature of thermogenic and biogenic methane, Science, Vol. 344, pp. 1500-1503).

In addition to the size of the signatures, the time required for these processes to affect the signature may also differ from compound to compound. Integration of measured multiply substituted isotopologue signatures and position specific isotope signatures of multiple hydrocarbon species with an understanding of the kinetic properties of these species provides unique constraints on both the temperature at which hydrocarbons are generated or stored in the subsurface and the length of time these hydrocarbons have been stored.

Kinetic properties of multiply substituted isotopologues signatures and position specific isotope signatures may be derived from laboratory experiments or modeling approaches. For example, some species may develop a signature that does not change over timescales of billions of years if conditions or reactions change. One example of this may be methane, which appears to develop a multiply substituted isotopologue signature that is dominantly sensitive to temperature. This signature appears to develop during generation of the methane, and is then locked in or retained even if the methane is transported to a colder environment and stored (See, e.g., (2014), Stolper et al., Formation temperature of thermogenic and biogenic methane, Science, Volume 344, pp. 1500-1503). That is, the reaction for methane to change at different temperature is too slow to have any impact over the time scale of interest (e.g., the change may involve one or more billion years). In contrast, other molecules that are sensitive to temperature may track changes in temperature over short timescales. For example, decane may initially develop a signature that records the temperature at which it was generated, but this signature may subsequently change to reflect increases or decreases in the temperature at which the compound resides over timescales of years. By measuring the clumped and position specific isotope signatures of multiple hydrocarbon compounds that have different rates of reaction, different information about the history of the hydrocarbons following generation may be determined. The hydrocarbon generation, entrapment and/or storage temperatures derived from the measured signatures are then integrated with a basin model of the area of interest, which can be used to constrain the time at which the hydrocarbons in the source and/or reservoir reached these temperatures. This information can then be integrated alongside other contextual information to constrain timing of certain hydrocarbon system components, which can be used to address questions in hydrocarbon system analysis and lessen uncertainty. Various aspects of the present techniques are described further in FIGS. 1 to 6.

FIG. 1 is a side elevational diagram 100 of components of a hydrocarbon system in a subsurface region. In this diagram 100, components and processes in a hydrocarbon system are provided for a subsurface region 102, which are at least partially below a body of water 104. The processes of a hydrocarbon system involve generation, migration, trap formation, accumulation or leakage to a seep, and/or preservation. The components of the hydrocarbon system include various portions of a formation, such as source rocks 106, reservoir rocks 108, and seal rocks 110. Hydrocarbon system analysis may involve determining source presence, source maturation, trap presence, migration pathways, reservoir presence, trap seal presence and timing. The hydrocarbons may be produced through a wellbore 126.

As an example, the hydrocarbon system process may involve various steps to form current hydrocarbon accumulation locations. First, hydrocarbons are generated, which occurs in source rock 106. Then, the hydrocarbons migrate from the source rock 106 through faults and fractures, such as fractures 111, as shown by arrows 112, 114, 116 and 118. Hydrocarbons accumulate in a reservoir. Accumulation of hydrocarbons can only occur if a trapping structure is present at the same time or before hydrocarbons migrate through the reservoir rock 108 if an adequate seal rock 110 is in place. Hydrocarbons can be stored in an accumulation and preserved, as shown by the seal rocks 110 or may be altered by a fracture, as shown by fault 120. If limited by subsurface geology, the hydrocarbons may be trapped in hydrocarbon accumulations, such as a gas reservoir and/or an oil/gas reservoir. Hydrocarbons may exit the subsurface, for example by seeping into the body of water 104 via the fault 120, as shown by bubbles 122, and form an oil slick 124 on the surface of the body of water 104.

The signatures measured from hydrocarbons may be integrated according to disclosed methodologies and techniques herein to address components in hydrocarbon system analysis. In particular, the present techniques may determine the presence and level of thermal maturity of source(s) of hydrocarbons in the subsurface as well as presence and timing of trap and seal components. If the presence of source rocks, extent of maturation, timing of migration or trap or seal presence and the efficiency of trapping can be determined, it is possible to develop or refine exploration, development, and production strategies for more efficient capture and production of subsurface hydrocarbons accumulations.

Figure 2:
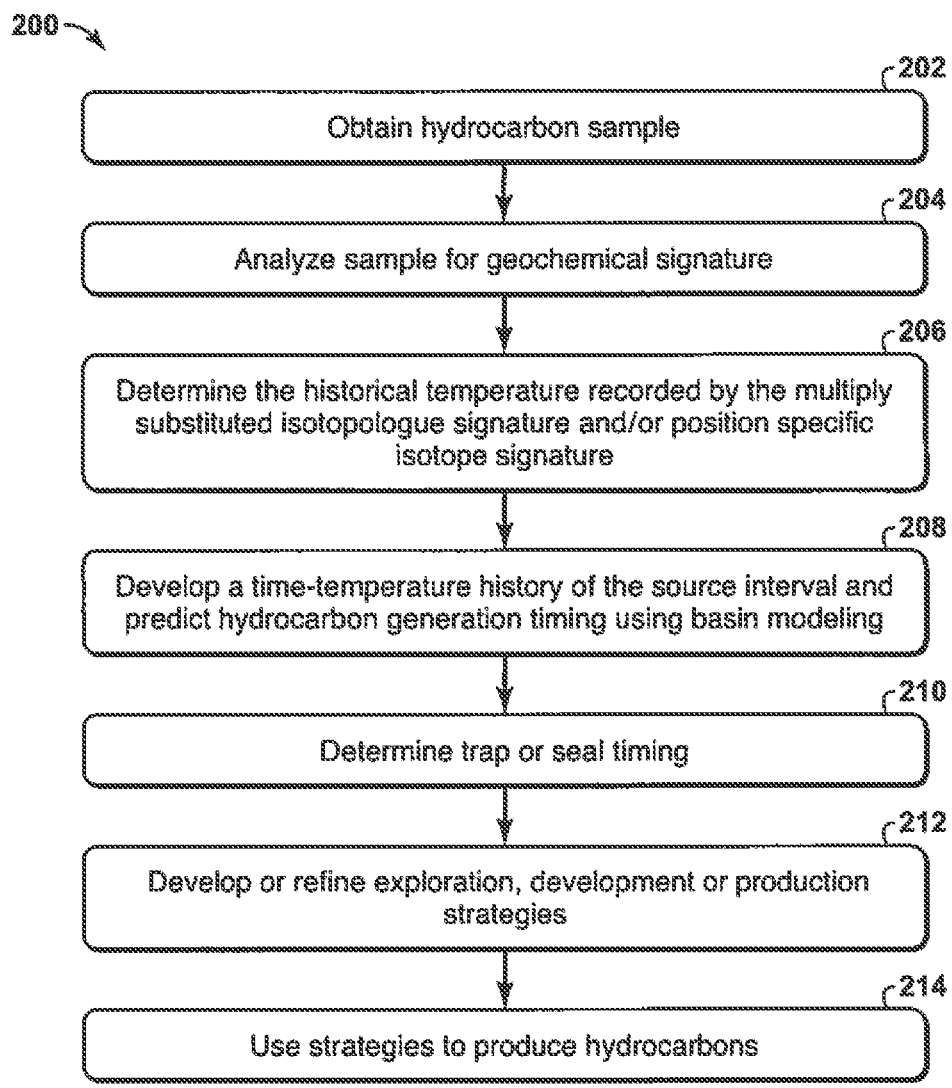
FIG. 2 is a flow diagram of a method for determining trap and adequate seal timing in accordance with an exemplary embodiment of the present techniques.

As one example, in hydrocarbon system where there is adequate charge and migration is assumed to be instantaneous, the generation temperature of hydrocarbons may serve as a proxy for the time at which a trap and effective seal was present and the time at which hydrocarbons started accumulating, which is discussed further in FIG. 2.

FIG. 2 is a flow diagram 200 of a method for determining trap and adequate seal timing in accordance with an exemplary embodiment of the present techniques. In this flow diagram 200, various steps are performed to that utilize multiply substituted isotopologue signature and/or position specific isotope signature to determine the time-temperature history of the source to predict hydrocarbon generation.

At block 202, a sample of hydrocarbons is obtained. This sample may be in the form of oil and/or gas obtained from the subsurface, at a surface location, such as a seep, and may be in the form of free oil or gas or may be trapped within a rock sample.

At block 204, the sample is analyzed for geochemical signatures. The geochemical signatures include multiply substituted isotopologue signature and/or position specific isotope signature. The geochemical signatures may also comprise bulk composition, isotopic signatures, molecular geochemistry, multiply substituted isotopologue and or position specific isotope geochemistry, and physical parameters such as freezing or boiling points of a given compound. For example, if methane, the primary chemical component of natural gases, it is possible to investigate the potential of forming the clumped doubly substituted isotopologue $^{13}CH_3D$, and the doubly substituted isotopologue $^{12}CH_2D_2$. The measurement of the absolute abundance of isotopologues for any given hydrocarbon involves knowledge of the molecular mass at which they are present, and involves knowledge of the actual identity of each possible isotopologue for that species. Measurement of the abundance of each isotopologue and fragment for position specific isotope determination can be conducted using multiple techniques such as mass spectrometry and/or laser-based spectroscopy.

Then, at block 206, the historical temperature recorded by the multiply substituted isotopologue signature and/or position specific isotope signature is determined for any given hydrocarbon. Historical temperature is an equilibrium signature that can be predicted by molecular modeling of equilibrium concentrations of multiply substituted isotopologues or positional effects, or may be determined empirically by measurements of signatures of a given hydrocarbon compound at different temperatures either in the presence or absence of a catalyst to accelerate equilibrium. Different hydrocarbon species have different rates of equilibration in multiply substituted isotopologues. For example, methane records methane generation temperature and preserves this signature even when exposed to different temperatures. In contrast, a molecule such as decane may give a historical temperature that reflects the temperature at which it has been stored over the past several years because it can undergo intra-molecular isotope exchange over faster timescales than methane. Historical temperatures obtained from the clumped or position specific isotope signatures may be different for different species because each of these hydrocarbon compounds record different parts of the history of the bulk hydrocarbon given their different kinetic behaviors.

In block 208, a time-temperature history is developed for the source interval and the hydrocarbon generation timing is predicted using basin modeling. The source interval may include source rock that is potentially present in the subsurface using basin modeling approaches. Source rock maturity may be known if source rocks are penetrated and sampled during drilling activities. Accordingly, these approaches should be calibrated with direct temperature information (e.g., from fluid inclusion temperatures) or indirect maturity information (e.g., vitrinite, molecular geochemistry etc.). From this thermal history, the timing of hydrocarbon generation can be predicted using maturation models. See, e.g., Sweeney and Burnham, Evaluation of a simple model of vitrinite reflectance based on chemical kinetics, AAPG Bulletin, Vol. 74, No. 10, pp. 1559-1570, 1990.

In block 210, the trap or sealing timing is determined. The time at which an effective trap or adequate seal was in place that has trapped the accumulated hydrocarbons may be determined from different approaches.

As one example, the trap or sealing timing may be determined by comparison of a measured multiply substituted isotopologue temperature that does not equilibrate following generation (e.g., methane) with the calculated volume weighted average temperature that arises assuming that all hydrocarbons are trapped following generation. A volume weighted average temperature can be determined for any given hydrocarbon compound by calculating the volume of hydrocarbons generated at each time-temperature interval as a function of the time-temperature history. From this calculation, the average temperature of hydrocarbon generation can be calculated by multiplying the temperature by the volume produced at that temperature and dividing by the total volume of hydrocarbons generated. This initial temperature may be the average generation temperature, which may be recorded for example in methane. If the measured and modeled average temperatures match, then the trap and an adequate seal have been present at least at the time of hydrocarbon generation initiation. If the measured and modeled average temperatures do not match, then a statistical technique can be used to determine the temperature at which hydrocarbons began or finished accumulating. The temperature at which hydrocarbons begin accumulating, as determined from this process, can be converted to a time by using the time-temperature history developed in block 208 and is the latest point at which an adequate trap and seal could be present.

As a second example, the trap or sealing timing may be determined by determining the minimum residence time of the fluids through comparison of the multiply substituted isotopologue temperatures of different hydrocarbon compounds and statistical techniques (such as, forward or inverse modeling) to calculate the residence time of these fluids given an initial starting temperature of hydrocarbon generation (given either from calculation of the volume weighted average temperature of generation as per the above example, or through measurement of the temperature of a hydrocarbon that does not equilibrate following generation) through knowledge of the kinetic behavior of different compounds. Rates of equilibration, or the kinetic behavior, for different hydrocarbon species can be determined through molecular modeling approaches. Given a known measured present day temperature for any given compound obtained in block 206, an initial temperature of generation determined above, and a quantified rate of equilibration, the time required to get to the current day temperature may be determined using multiple approaches that may comprise an inverse modeling approach. This can be repeated for each temperature obtained for a hydrocarbon in block 206 to obtain a potential range in residence times. This range in residence time is therefore the minimum point at which an effective trap and adequate seal have been present to develop the present day hydrocarbon accumulation.

In block 212 an exploration, development, and/or production strategy is developed or refined using information obtained in block 210. For example, one can use information about known trap and seal timing, and there relative timing with respect to source rock maturation, to determine the events which gave rise to these trapping and structures and seals regionally. Given knowledge of the regional controls on trap and seal timing and an understanding of when source rocks began generating in the region, other prospects and structures that may pre-date, are co-incident with or post-date the trapping structures determined in block 210 may be targeted to further explore and develop for hydrocarbons.

These strategies may then be used to produce hydrocarbons from the subsurface accumulations in block 214. Producing hydrocarbon may include operations, such as modeling the location to drill a well, directing acquisition of data for placement of a well, drilling a well, building surface facilities to produce the hydrocarbons, along with other operations conducted in and/or associated with the well after the well is completed. Accordingly, producing hydrocarbons includes hydrocarbon extraction, along with injection of gas or liquid for increasing drive pressure, mobilizing the hydrocarbon or treating by, for example chemicals or hydraulic fracturing the wellbore to promote increased flow, well servicing, well logging, and other well and wellbore treatments.

As an example, the $^{13}$C-D multiply substituted isotopologue signature of methane records methane generation temperature. Biogenic methane gas may be generated over a temperature interval of 0 to 80° C. A thermal history of a particular reservoir or source unit can be estimated using a calibrated basin model. Basin modeling may be used to calculate how much biogenic gas is produced at a given temperature and/or over a time-temperature history. This results in a time-temperature distribution of gas formation from which an average gas generation temperature can be calculated for the total gas volume. This can then be compared with the methane multiply substituted isotopologue temperature that records methane generation temperature. If the two temperatures are different, a statistical model can be used to determine what minimum and maximum trapping temperature for the bulk gas volume is involved to account for the measured methane temperature. From this calculation or information, a time of seal formation or trap competency can be determined.

As another example, a similar process can be used to constrain seal timing in thermogenic systems. In this example, hydrocarbons that retain a generation temperature over timescales of accumulation can be used to constrain seal timing. In thermogenic systems, however, additional constraints provided by multiply substituted isotopologue, position specific effect measurements and the associated kinetic properties of higher hydrocarbons (not produced in biogenic gases) provides an independent verification on temperature-time. Smaller hydrocarbons preserve generation temperatures for longer timescales and provide constrains on maturation timing, while co-existing larger hydrocarbons that equilibrate to reservoir temperatures over shorter timescales can also be used to bracket residence times of hydrocarbons within the accumulations.

As another example of how an enhanced hydrocarbon system analysis can be used to develop or refine exploration, development, or production strategies, if trap timing is known and precedes maturation timing, the integration of multiply substituted isotopologue or position specific effect temperatures of hydrocarbons with basin modeling may be used to infer generation timing or the efficiency with which the trap has accumulated hydrocarbons.

Figure 3:
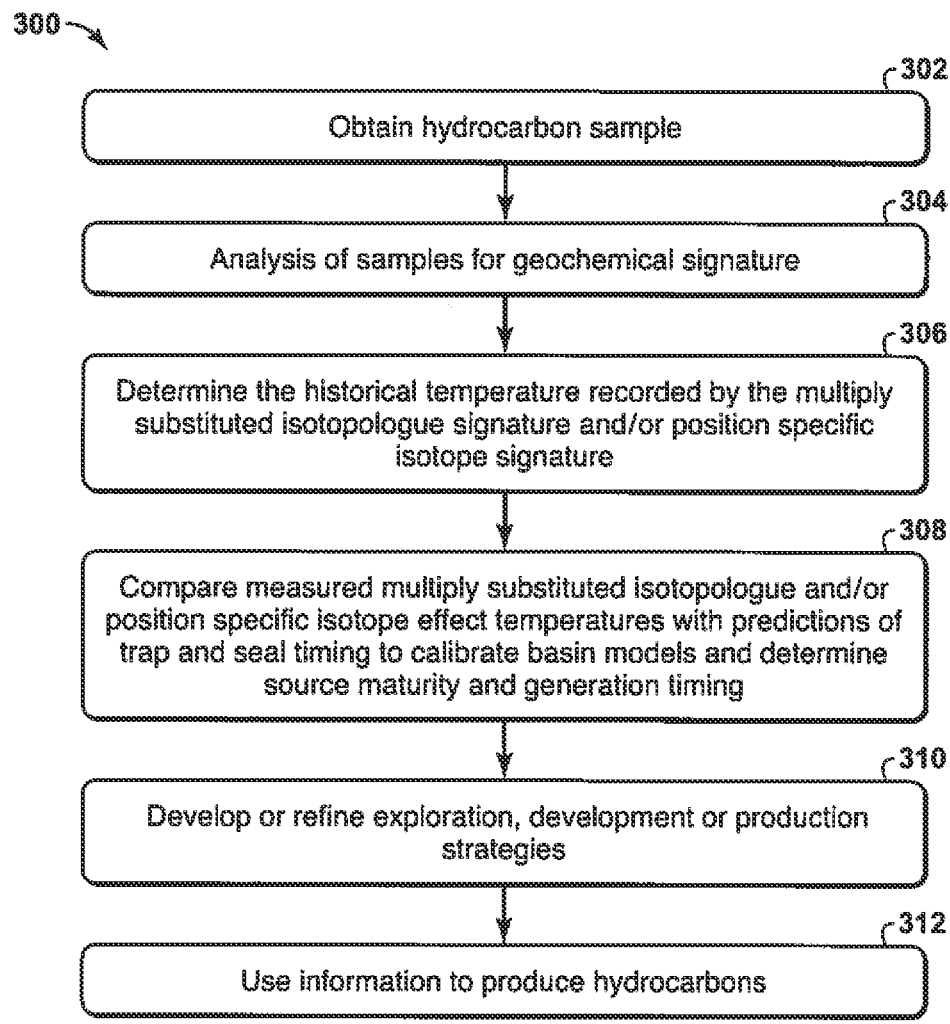
FIG. 3 is a flow diagram of a method for determining source maturity and maturation timing in accordance with an exemplary embodiment of the present techniques.

FIG. 3 is a flow diagram 300 of a method for determining source maturity and maturation timing in accordance with an exemplary embodiment of the present techniques. In this flow diagram 300, various steps are performed to that utilize multiply substituted isotopologue signature and/or position specific isotope signature to determine the source maturity and maturation timing to predict hydrocarbon generation.

The method begins at block 302. In block 302, a sample of hydrocarbons is obtained. This sample can be in the form of oil and/or gas obtained from the subsurface, at a surface location such as a seep, and is in the form of free oil or gas or may be trapped within a rock sample, which may be similar to block 202 of FIG. 2.

At block 304, the sample is analyzed for geochemical signatures. Similar to the discussion of block 204 of FIG. 2, the geochemical signatures may comprise bulk composition, isotopic signatures, molecular geochemistry, multiply substituted isotopologue and or position specific isotope geochemistry, and physical parameters such as freezing or boiling points of a given compound. If methane, the primary chemical component of natural gases, is used as an example, it is possible to investigate the potential of forming the clumped doubly substituted isotopologue $^{13}$CH$_3$D, and the doubly substituted isotopologue $^{12}$CH$_2$D$_2$. The measurement of the absolute abundance of isotopologues for any given hydrocarbon involves knowledge of the molecular mass at which they are present, and involves knowledge of the actual identity of each possible isotopologue for that species. Measurement of the abundance of each isotopologues and fragment for position specific isotope determination can be conducted using multiple techniques, such as mass spectrometry and/or laser-based spectroscopy.

In block 306, the historical temperature recorded by the multiply substituted isotopologue signature and/or position specific isotope signature is determined for any given hydrocarbon. This determination may be performed similar to the calculations noted above in block 206 of FIG. 2.

In block 308, the determined temperature is considered along with information on when the trap and seal were present and effective to determine the maturity of a source rock and determine hydrocarbon generation timing. Constraints on the timing of trap presence can be provided, for example, by observations from surface geology or interpretations of geophysical data (e.g., seismic reflection data) that provide relative timing of deformation in the subsurface. Biostratigraphy analysis may also be used to age date particular lithologies, so that the information from relative timing of structure deformation can be converted to an absolute time scale. Constraints on adequate seal timing can be provided by, for example, determining the depth to which rocks have to be buried to develop sufficient competence to hold and store a given column height of hydrocarbons within an underlying structure.

The historical temperatures derived in block 306 are then used to determine the present day temperature or, if the temperature has been higher in the past, the maximum burial temperature. This can be done by considering the temperature of a compound that preserves generation temperature (e.g., methane) or by back calculating initial generation temperature from a known present day temperature, a thermal history for that reservoir, and the kinetics associated with isotope exchange and temperature sensitivity for any given compound.

The temperature provided by the multiply substituted isotopologue and/or position specific effect measurement is the volume weighted average temperature, which represents a mixture of gases produced over some temperature range. The minimum and maximum gas generation temperatures reflected in the volume weighted average temperature may be determined using different approaches. One such approach may include assuming the minimum temperature at which any gas is likely to have been generated (e.g., 90° C.) and iteratively add gas volumes generated as a function of increases in temperature (such information on hydrocarbon yield can be provided from maturation and thermal cracking models from basin modeling approaches) until the volume weighted average temperature matches the measured temperature. The maximum temperature to provide the measured multiply substituted isotopologue temperature is thereby the final temperature reached using this iterative approach. Alternatively, a statistical technique (e.g. inverse modeling) can be used as a second approach. In this approach, the maximum temperature experienced is determined by considering the present day temperature, assuming a starting temperature of gas generation, and de-convolving contributions of gas on a volume-temperature related basis to calculate the maximum temperature experienced.

A second approach is to measure multiple samples that likely preserve subtly different mixtures of gases with different minimum and maximum temperatures. These signatures can then be plotted on a simple figure to define a mixing line. A statistical inversion technique can then be used to determine the absolute minimum and maximum temperatures that have contributed hydrocarbons to the sample. For example, different mixtures of gas histories may be obtained from comparing temperatures from hydrocarbons present in fluid inclusions (which preserve a record of gas composition from some time prior to present day) with those present in free hydrocarbon phases. Additional analysis of the fluid inclusions to provide gas inclusion composition or fluid API, for example, can also be integrated with temperatures derived from multiply substituted isotopologues or position specific isotope effects to further constrain hydrocarbon generation timing. In the instance that water inclusions are also present, differences in trapping temperatures from fluid inclusions with temperatures from hydrocarbon compounds (corrected for isotope exchange reactions over a time-temperature history given equilibration rates for that compound in some hydrocarbons or not for those that preserve generation temperature) can be interpreted to constrain and calibrate thermal histories to determine hydrocarbon generation timing.

Further, a third approach may involve analyzing the historical temperatures provided in block 306 of multiple hydrocarbon compounds. Knowledge of the kinetic behavior or rates of equilibration of these different compounds can be used alongside a thermal history to back calculate initial volume weighted average generation temperatures of the different compounds. From this mixture, the minimum and maximum gas generation temperatures reflected in the volume weighted average temperature using different approaches, as described above, may be determined.

Then, once the present day or previous maximum burial temperature has been determine, the time at which hydrocarbons began generating can be determined. This calculation may involve integrating maximum burial temperatures with knowledge of hydrocarbon maturation kinetics (e.g., provided by models, such as Sweeney and Burnham, 1989) and time-temperature histories provided by basin modeling approaches.

In block 310, an exploration, development, and/or production strategy is developed using information obtained in 308. For example, the information about known maturity and maturation timing may be used along with the relative timing with respect to trap and seal, to identify which structures were in place prior to maturation and hydrocarbon charge. Given knowledge of the relative difference between maturation timing and trap and seal timing locally and regionally, other prospects and structures may be targeted, which are likely to host hydrocarbon accumulations for further exploration and development.

These strategies may then be used to produce hydrocarbons from the subsurface accumulations in block 312. The production of hydrocarbons may be similar to the discussion of block 214 of FIG. 2.

As another example of how an improved hydrocarbon system analysis can be used to develop or refine exploration, development, or production strategies, if maturation timing is known or can be predicted for each source rock potentially present in the subsurface, multiply substituted isotopologue or position specific effect temperatures of hydrocarbons measured from samples may be used to determine the source that generated the sampled hydrocarbons when multiple sources are present. Given some understanding on likely source type, this may be used to infer regional potential for further oil and gas accumulations.

Figure 4:
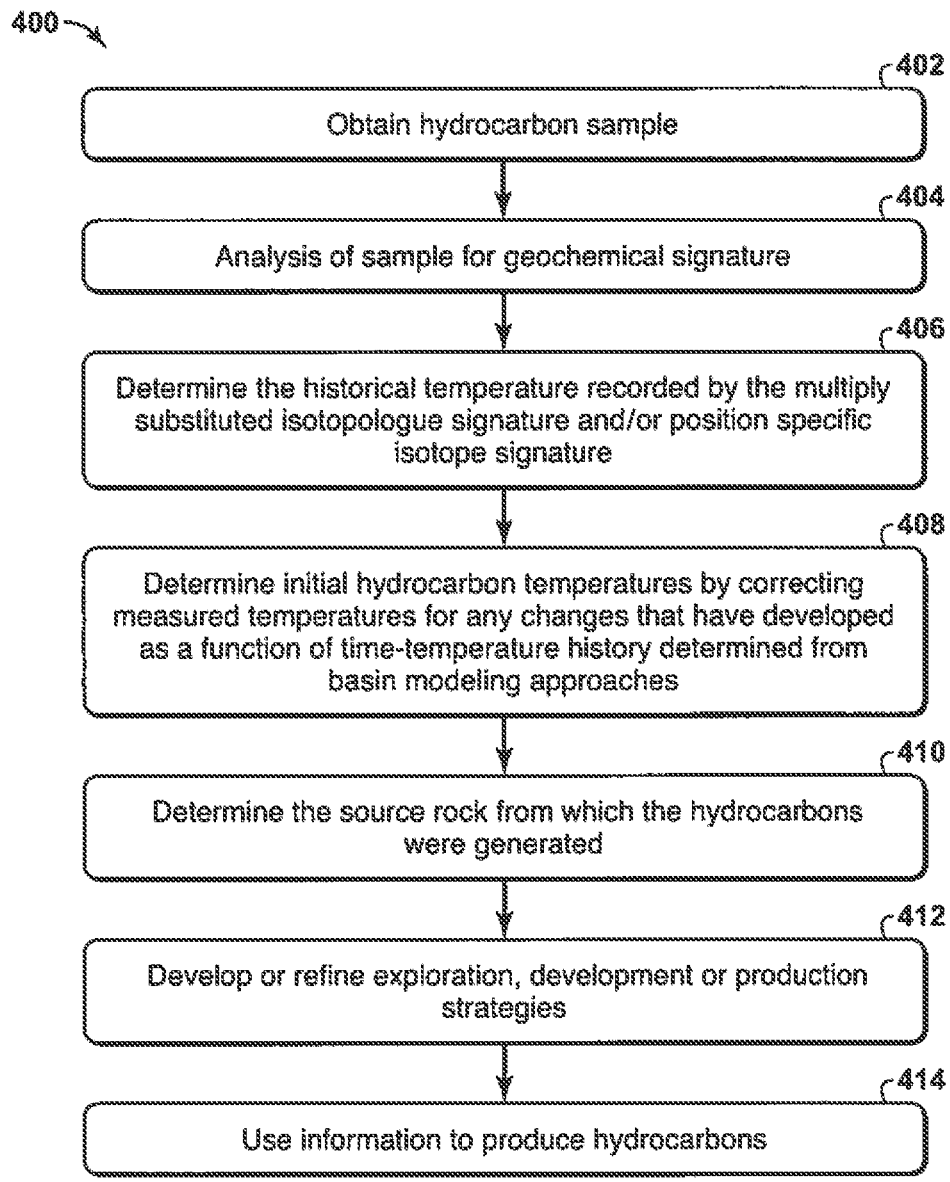
FIG. 4 is flow diagram of a method for determining the source of hydrocarbons in the subsurface in accordance with an exemplary embodiment of the present techniques.

FIG. 4 is a flow diagram 400 of a method for determining the source of hydrocarbons in the subsurface in accordance with an exemplary embodiment of the present techniques. In this flow diagram 400, various steps are performed to that utilize multiply substituted isotopologue signature and/or position specific isotope signature to determine the source of hydrocarbons in the subsurface.

In block 402, a sample of hydrocarbons is obtained. This sample can be in the form of oil and/or gas obtained from the subsurface, at a surface location (e.g., a seep), and is in the form of free oil or gas or is trapped within a rock sample, which may be similar to block 202 of FIG. 2.

At block 404, the sample is analyzed for a variety of geochemical signatures. Similar to block 204 of FIG. 2, the geochemical signatures may include bulk composition, isotopic signatures, molecular geochemistry, multiply substituted isotopologue and or position specific effect geochemistry, and physical parameters such as freezing or boiling points of a given compound. If methane, the primary chemical component of natural gases, is used as an example, it is possible to investigate the potential of forming the clumped doubly substituted isotopologue $^{13}CH_3D$, and the doubly substituted isotopologue $^{12}CH_2D_2$. The measurement of the absolute abundance of isotopologues for any given hydrocarbon requires knowledge of the molecular mass at which they are present, and hence requires knowledge of the actual identity of each possible isotopologue for that species. Measurement of the abundance of each isotopologues and fragment for position specific isotope determination can be conducted using multiple techniques such as mass spectrometry and/or laser-based spectroscopy.

Then, in block 406, the historical temperature recorded by the multiply substituted isotopologue signature and/or position specific isotope signature is determined for any given hydrocarbon. This determination may be similar to the determination made in block 206, as noted in FIG. 2.

In block 408, the initial hydrocarbon temperatures may be determined by correcting measured temperatures for any changes that have developed as a function of time-temperature history determined from basin modeling approaches. The historical temperatures derived in block 406 may be used to determine the present day temperature or, if the temperature has been higher in the past, the maximum temperature experienced by any hydrocarbon compound. This determination may be performed based on the temperature of a compound that preserves generation temperature (e.g. methane) or by back calculating initial generation temperature from a known present day temperature, a thermal history for that reservoir, and the kinetics associated with isotope exchange and temperature sensitivity for any given compound.

As described above, the temperature provided by the multiply substituted isotopologue or position specific effect measurement is the volume weighted average temperature, which represents a mixture of gases produced over some temperature range. One can determine the minimum and maximum gas generation temperatures reflected in the volume weighted average temperature using different approaches. Examples of such approaches are noted above in the discussion associated with block 308.

In block 410, the source rock from which the hydrocarbons were generated is determined. This determination may include using the maximum temperature that has been determined for each hydrocarbon compound in block 408 and comparing this maximum temperature to modeled volume weighted hydrocarbon temperatures for different compounds for each source rock that is present in the subsurface. Based on this comparison a determination is made as to which source rock produced the hydrocarbons sampled. This comparison may be performed using multiple approaches. One approach may include using basin modeling approaches to determine a time-temperature history for the source rock. Then, the volume weighted average temperature can be modeled for each compound by considering the volume of hydrocarbons generated as a function of time and temperature for each source rock (e.g., provided by models such as Sweeney and Burnham, 1989), a time-temperature history for the source rock and from data for the rates of equilibration for each hydrocarbon compound considered.

In some situations, multiple source rocks may have produced hydrocarbons. In such examples, statistical models can be used to calculate volume weighted average temperatures for each hydrocarbon compound when the sample represents a mixture of differently sourced hydrocarbons. Relative timing of source rock maturation can be used alongside knowledge of trap timing to model mixtures from the different source intervals.

Consideration of temperatures in block 410 can also be performed in conjunction with other geochemical techniques, such as molecular geochemistry, which may be used to determine the maturity and source facies of the source rock that generated the hydrocarbons. They may also be used to determine geologic ages if biomarkers unique to specific time periods can be identified in the hydrocarbon sample. This information can then be used to determine the most likely source rock to have produced the hydrocarbons.

In block 412, an exploration, development, or production strategy is developed or refined. The development or refinement may involve using information obtained in block 408. For example, the information about which source interval is mature and producing hydrocarbons may be utilized to predict fluids that are likely to be present elsewhere in a basin. Further, if an oil prone source rock is shown to be mature and producing gas, while a shallower gas prone source rock is shown to be not contributing significant volumes of gas to the sample analyzed, an exploration strategy may be developed to explore for the deeper source rock to be producing oil at shallower depths elsewhere in the basin that is subsequently stored in accumulations. Therefore, given knowledge of the source of hydrocarbons carbons within a basin and the relative maturities and volumes of hydrocarbons generated from these different source rocks, other prospects and structures that are more likely to host hydrocarbon accumulations to may be targeted to further explore and develop the subsurface regions.

These strategies may then be used to produce hydrocarbons from the subsurface accumulations in block 414. The production of hydrocarbons may be similar to the discussion of block 214 of FIG. 2.

Figure 5:
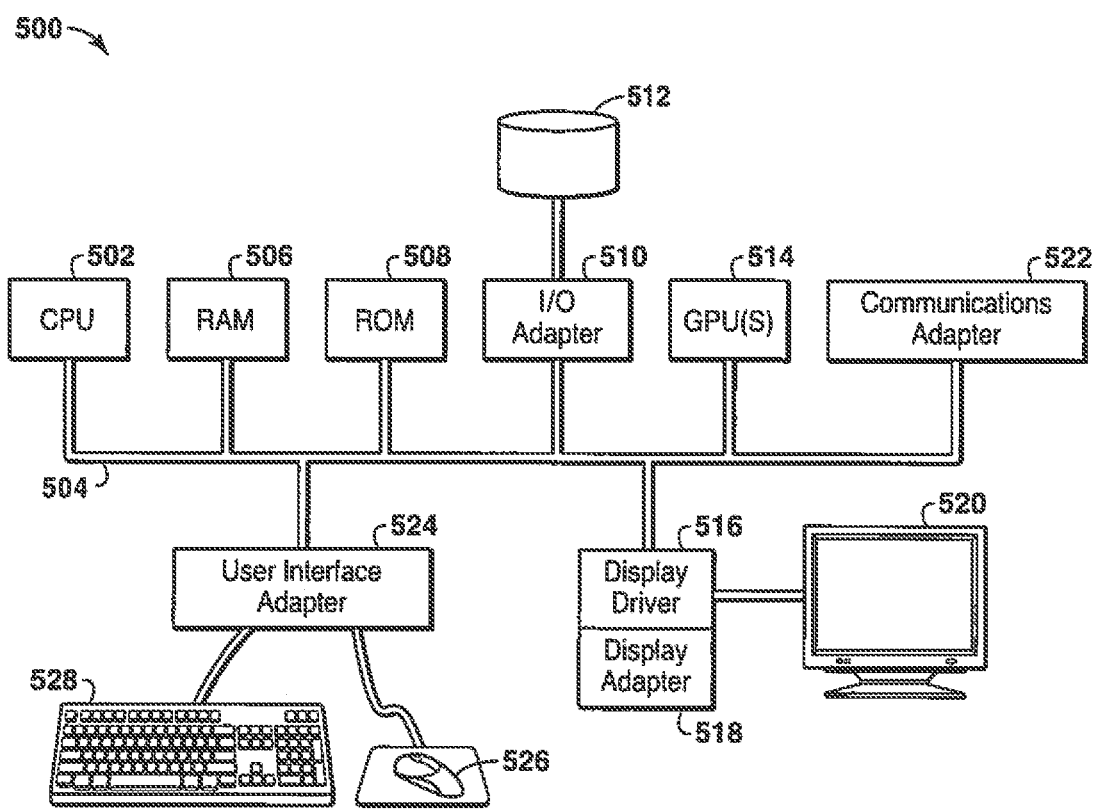
FIG. 5 is a block a diagram of a computer system in accordance with an exemplary embodiment of the present techniques.

FIG. 5 is a block diagram of a computer system 500 in accordance with an exemplary embodiment of the present techniques. A central processing unit (CPU) 502 is coupled to system bus 504. The CPU 502 may be any general-purpose CPU, although other types of architectures of CPU 502 (or other components of exemplary system 500) may be used as long as CPU 502 (and other components of system 500) supports the inventive operations as described herein. The CPU 502 may execute the various logical instructions according to various exemplary embodiments. For example, the CPU 502 may execute machine-level instructions for performing processing according to the operational flow described above.

The computer system 500 may also include computer components such as a random access memory (RAM) 506, which may be SRAM, DRAM, SDRAM, or the like. The computer system 500 may also include read-only memory (ROM) 508, which may be PROM, EPROM, EEPROM, or the like. RAM 506 and ROM 508 hold user and system data and programs, as is known in the art. The computer system 500 may also include an input/output (I/O) adapter 510, a communications adapter 522, a user interface adapter 524, and a display adapter 518. The I/O adapter 510, the user interface adapter 524, and/or communications adapter 522 may, in certain embodiments, enable a user to interact with computer system 500 in order to input information.

The I/O adapter 510 preferably connects a storage device(s) 512, such as one or more of hard drive, compact disc (CD) drive, floppy disk drive, tape drive, etc., to computer system 500. The storage device(s) may be used when RAM 506 is insufficient for the memory requirements associated with storing data for operations of embodiments of the present techniques. The data storage of the computer system 500 may be used for storing information and/or other data used or generated as disclosed herein. The communications adapter 522 may couple the computer system 500 to a network (not shown), which may enable information to be input to and/or output from system 500 via the network (for example, the Internet or other wide-area network, a local-area network, a public or private switched telephony network, a wireless network, any combination of the foregoing). User interface adapter 524 couples user input devices, such as a keyboard 528, a pointing device 526, and the like, to computer system 500. The display adapter 518 is driven by the CPU 502 to control, through a display driver 516, the display on a display device 520. Information and/or representations pertaining to a portion of a supply chain design or a shipping simulation, such as displaying data corresponding to a physical or financial property of interest, may thereby be displayed, according to certain exemplary embodiments.

The architecture of system 500 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

For example, the computer system 500 may include a processor; memory in communication with the processor; and a set of instructions stored in memory and accessible by the processor. The set of instructions may be used to determine hydrocarbon system process, such as seal timing or trap timing and may be used to provide or display an exploration, development, or production strategy. The set of instructions, when executed by the processor, may be configured to: analyze a hydrocarbon sample associated with a subsurface source interval for a geochemical signature, wherein the geochemical signature comprises a multiply substituted isotopologue signature and/or a position specific isotope signature for a one or more specific hydrocarbon compound; determine one or more historical temperatures based on the multiply substituted isotopologue signature and/or position specific isotope signature; define one or more of seal timing, trap timing, migration efficiency and charge efficiency based on the determined one or more historical temperatures; and develop or refine an exploration, development, or production strategy based on the defined one or more of seal timing, trap timing, migration efficiency and charge efficiency.

In other embodiments, the computer system may include set of instructions that are configured to perform other operations. For example, the set of instructions may be configured to determine one or more historical temperatures, are further configured to: compare methane isotopes to a different hydrocarbon isotope to compare temperature equilibration rates. Also, the set of instructions may be configured to develop a time-temperature history of the source interval or a reservoir interval; compare the one or more historical temperatures with model temperatures predicted using a basin model; and determine the timing of the one or more of seal timing, trap timing, migration efficiency and charge efficiency from the comparison. Also, the set of instructions that are configured to perform maturation modeling using a basin model calibrated from one or more of fluid inclusion temperatures and indirect maturity information about the source interval.

Further, in other embodiments, the set of instructions may include other features. For example, the set of instructions may be configured to develop a time-temperature history of the source interval; determine timing of hydrocarbon generation from the source interval using a basin model; and determine seal timing by comparing at least one of the one or more historical temperatures with at least one of model average gas generation temperatures predicted using a basin model or through determination of a residence time of hydrocarbons in a reservoir interval. Also, the set of instructions may be configured to develop a time-temperature history of the source interval; determine timing of hydrocarbon generation from the source interval using basin modeling; and determine trap timing by at least one of comparing at least one of the one or more historical temperatures with at least one of model average gas generation temperatures predicted using a basin model or through determination of the residence time of hydrocarbons in a reservoir interval. Further still, the instructions may be configured to: compare a present day measured multiply substituted isotopologue temperature that provides generation temperature with a modelled generation temperature calculated from the basin model based on a determined volume weighted average gas generation temperature; and/or determine a minimum residence time of hydrocarbons through comparison of the present day multiply substituted isotopologue temperatures of different hydrocarbon compounds and statistical techniques to calculate the residence time of the hydrocarbons given an initial starting temperature of hydrocarbon generation through knowledge of the kinetic behavior of different compounds. Moreover, the set of instructions may be configured to: predict trap and seal timing with a basin model; compare the determined temperatures with predictions of trap and seal timing to calibrate the basin model and to determine source maturity and generation timing.

Figure 6:
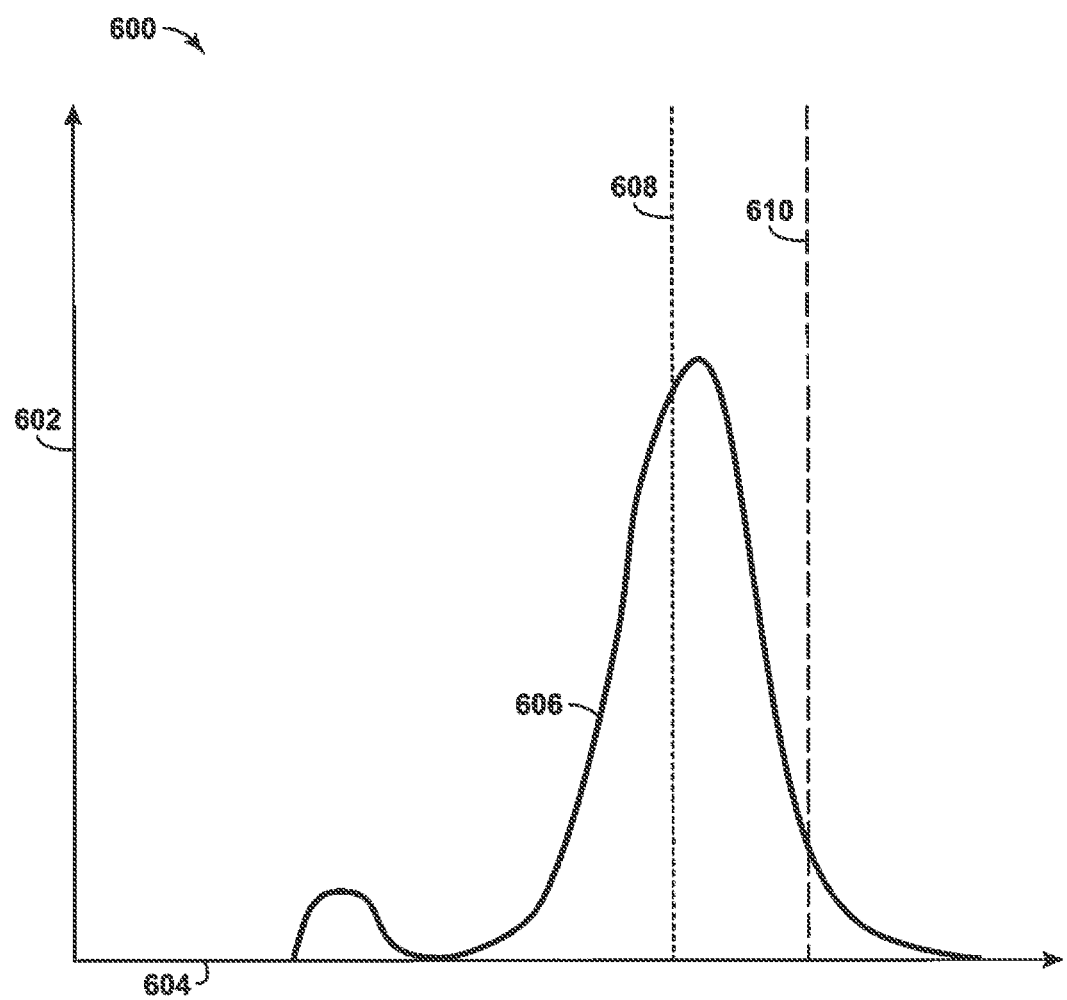
FIG. 6 is a graph of a hydrocarbon volume generation profile in accordance with an exemplary embodiment of the present techniques.

FIG. 6 is a graph 600 of a hydrocarbon volume generation profile in accordance with an exemplary embodiment of the present techniques. In this graph 600, a representative hydrocarbon yield profile response 606 is shown along a temperature axis 604 in degree C. and an incremental hydrocarbon yield produced by source rock axis 602 in Bbl or MScf/km$^2$ of source rock per million years. Also, a volume weighted average temperature of all gas produced calculated from this modeled hydrocarbon yield profile is shown along line 608 and a measured multiply substituted isotopologue or position specific isotope temperature is shown along line 610. The figure provides an example of how the modeled and measured temperatures may be compared in FIGS. 2 to 4. In graph 600, the measured temperature is greater than the modeled average temperature, which suggests that hydrocarbon produced during the early stages of maturation was either not trapped because there was no structure to store the hydrocarbon or was not stored because the seal was not of adequate integrity to maintain the pressure generated by the accumulated hydrocarbons. It could also be used to demonstrate the hydrocarbons generated did not originate from the source interval modeled in example of FIG. 4.

It should be understood that the preceding is merely a detailed description of specific embodiments of the invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other.

What is claimed is:

1. A method for exploration, production, and development of hydrocarbons comprising:
    obtaining a sample comprising hydrocarbons associated with a subsurface source interval;

analyzing the sample for a geochemical signature, wherein the geochemical signature comprises one or more of a multiply substituted isotopologue signature and a position specific isotope signature for a one or more specific hydrocarbon compound;

determining one or more historical temperatures based on the one or more of multiply substituted isotopologue signature and position specific isotope signature;

defining one or more of seal timing, trap timing, migration efficiency and charge efficiency based on the determined one or more historical temperatures; and developing or refining an exploration, development, or production strategy based on the defined one or more of seal timing, trap timing, migration efficiency and charge efficiency.

2. The method of claim 1, wherein determining the one or more historical temperatures comprises comparing methane isotopes to a different hydrocarbon isotope to compare temperature equilibration rates.

3. The method of claim 1, wherein defining the one or more of seal timing, trap timing, migration efficiency and charge efficiency based on the determined one or more historical temperatures comprises:

developing a time-temperature history of the source interval or a reservoir interval;

comparing the one or more historical temperatures with model temperatures predicted using a basin model; and determining the one or more of seal timing, trap timing, migration efficiency and charge efficiency based on the determined one or more historical temperatures from the comparison.

4. The method of claim 3, wherein developing the time-temperature history of the source or reservoir interval comprises using a basin model calibrated from one or more of fluid inclusion temperatures and indirect maturity information about the source interval.

5. The method of claim 1, wherein defining one or more of seal timing, trap timing, migration efficiency and charge efficiency is seal timing.

6. The method of claim 1, wherein defining one or more of seal timing, trap timing, migration efficiency and charge efficiency is trap timing.

7. The method of claim 1, wherein defining one or more of seal timing, trap timing, migration efficiency and charge efficiency comprises:

developing a time-temperature history of the source and/or reservoir interval;

determining timing of hydrocarbon generation from the source interval using basin modeling; and determining seal timing by comparing at least one of the one or more historical temperatures with at least one of model average gas generation temperatures predicted using a basin model or through determination of a residence time of hydrocarbons in the reservoir interval.

8. The method of claim 1, wherein defining one or more of seal timing, trap timing, migration efficiency and charge efficiency comprises:

developing a time-temperature history of the source and/or reservoir interval;

determining timing of hydrocarbon generation from the source interval; and determining trap timing by at least one of comparing at least one of the one or more historical temperatures with at least one of model average gas generation temperatures predicted using a basin model or through determination of the residence time of hydrocarbons in the reservoir interval.

9. The method of claim 8, wherein determining trap timing comprises comparing a present day measured multiply substituted isotopologue temperature that provides generation temperature with a modelled hydrocarbon generation temperature calculated from the basin model based on a determined volume weighted average hydrocarbon generation temperature.

10. The method of claim 8, wherein determining trap timing comprises determining a minimum residence time of hydrocarbons through comparison of the historical multiply substituted isotopologue temperatures of different hydrocarbon compounds and statistical techniques to calculate the residence time of the hydrocarbons given an initial starting temperature of hydrocarbon generation through knowledge of the kinetic behavior of different compounds.

11. The method of claim 1, wherein defining one or more of seal timing, trap timing, migration efficiency and charge efficiency comprises:

predicting trap and seal timing with a basin model;

comparing the determined temperatures with predictions of trap and seal timing to calibrate the basin model and to determine source maturity and generation timing.

12. The method of claim 1, wherein the geochemical signatures comprise one or more of bulk composition, isotopic signatures, molecular geochemistry, multiply substituted isotopologue geochemistry, position specific isotope geochemistry, and physical parameters.

13. The method of claim 1, further comprising producing hydrocarbons based on the exploration, development, or production strategy.

14. A computer system for exploration, production, and development of hydrocarbons comprising:

a processor;

memory in communication with the processor; and a set of instructions stored in memory and accessible by the processor, the set of instructions, when executed by the processor, are configured to:

analyze a hydrocarbon sample associated with a subsurface source interval for a geochemical signature, wherein the geochemical signature comprises one or more of a multiply substituted isotopologue signature and a position specific isotope signature for a one or more specific hydrocarbon compound;

determine one or more historical temperatures based on the one or more of multiply substituted isotopologue signature and position specific isotope signature;

define one or more of seal timing, trap timing, migration efficiency and charge efficiency based on the determined one or more historical temperatures; and develop or refine an exploration, development, or production strategy based on the defined one or more of seal timing, trap timing, migration efficiency and charge efficiency.

15. The computer system of claim 14, wherein the set of instructions that are configured to determine one or more historical temperatures, are further configured to: compare methane isotopes to a different hydrocarbon isotope to compare temperature equilibration rates.

16. The computer system of claim 14, wherein the set of instructions that are configured to define one or more of seal timing, trap timing, migration efficiency and charge efficiency, are further configured to:

develop a time-temperature history of the source and/or interval or a reservoir interval;

compare the one or more historical temperatures with model temperatures predicted using a basin model; and determine the timing of the one or more of seal timing, trap timing, migration efficiency and charge efficiency from the comparison.

17. The computer system of claim 16, wherein determining the timing of the one or more of seal timing, trap timing, migration efficiency and charge efficiency is determining the timing of seal timing or trap timing.

18. The computer system of claim 16, wherein the set of instructions that are configured to develop the time-temperature history of the source and/or reservoir interval, are further configured to: perform maturation modeling using a basin model calibrated from one or more of fluid inclusion temperatures and indirect maturity information about the source interval.

19. The computer system of claim 16, wherein the set of instructions that are configured to define one or more of seal timing, trap timing, migration efficiency and charge efficiency, are further configured to:

develop a time-temperature history of the source and/or reservoir interval;

determine timing of hydrocarbon generation from the source interval using a basin model; and determine seal timing by comparing at least one of the one or more historical temperatures with at least one of model average hydrocarbon generation temperatures predicted using a basin model or through determination of a residence time of hydrocarbons in a reservoir interval.

20. The computer system of claim 14, wherein the set of instructions that are configured to define one or more of seal timing, trap timing, migration efficiency and charge efficiency, are further configured to:

develop a time-temperature history of the source and/or reservoir interval;

determine timing of hydrocarbon generation from the source interval using basin modeling; and determine trap timing by at least one of comparing at least one of the one or more historical temperatures with at least one of model average hydrocarbon generation temperatures predicted using a basin model or through determination of the residence time of hydrocarbons in a reservoir interval.

21. The computer system of claim 20, wherein the set of instructions that are configured to determine trap timing, are further configured to: compare a present day measured multiply substituted isotopologue temperature that provides generation temperature with a modelled generation temperature calculated from the basin model based on a determined volume weighted average hydrocarbon generation temperature.

22. The computer system of claim 20, wherein the set of instructions that are configured to determine trap timing, are further configured to: determine a minimum residence time of hydrocarbons through comparison of the present day multiply substituted isotopologue temperatures of different hydrocarbon compounds and statistical techniques to calculate the residence time of the hydrocarbons given an initial starting temperature of hydrocarbon generation through knowledge of the kinetic behavior of different compounds.

23. The computer system of claim 14, wherein the set of instructions that are configured to define one or more of seal timing, trap timing, migration efficiency and charge efficiency, are further configured to:

predict trap and seal timing with a basin model;

compare the determined temperatures with predictions of trap and seal timing to calibrate the basin model and to determine source maturity and generation timing.

24. The computer system of claim 14, wherein the set of instructions that are configured to display the exploration, development, or production strategy.

* * * * *